United States Patent [19]

Rathbone et al.

[11] 4,442,123

[45] Apr. 10, 1984

[54] 6-CHLORO-6-DEOXY-D-HEXITOLS, COMPOSITIONS CONTAINING THEM AND THEIR USE IN FERTILITY CONTROL

[75] Inventors: Elner B. Rathbone, Wokingham; Geoffrey M. H. Waites, Reading; William C. L. Ford, Newbury, all of England

[73] Assignee: Tate & Lyle Public Limited Company, England

[21] Appl. No.: 334,550

[22] Filed: Dec. 28, 1981

Related U.S. Application Data

[63] Continuation of Ser. No. 124,461, Feb. 25, 1980, abandoned.

[30] Foreign Application Priority Data

Feb. 28, 1979 [GB] United Kingdom ................. 7907089
Mar. 12, 1979 [GB] United Kingdom ................. 7908627

[51] Int. Cl.$^3$ ..................... A01N 37/10; A01N 31/00; A61K 31/235; A61K 31/045

[52] U.S. Cl. .................................. 424/308; 424/311; 424/343; 424/305; 568/844; 560/111; 560/112; 560/214

[58] Field of Search ................. 568/844; 560/111, 112, 560/264; 424/305, 308, 311, 343

[56] References Cited

FOREIGN PATENT DOCUMENTS 15652 9/1980 European Pat. Off. ............ 568/844

OTHER PUBLICATIONS

Szafranek et al., J. of Chromatography, 161, (1978), 213–221.

*Primary Examiner*—Howard T. Mars
*Attorney, Agent, or Firm*—Ostrolenk, Faber, Gerb & Soffen

[57] ABSTRACT

6-Chloro-6-deoxy-D-hexitols, a novel class of compounds, and their esters, possess male antifertility activity and are thus useful in antifertility compositions. They are prepared by reduction of 6-chloro-6-deoxy-D-hexoses.

6 Claims, No Drawings

6-CHLORO-6-DEOXY-D-HEXITOLS, COMPOSITIONS CONTAINING THEM AND THEIR USE IN FERTILITY CONTROL

This is a continuation of application Ser. No. 124,461, filed on Feb. 25, 1980 abandoned.

This invention relates to chemical compositions possessing male fertility-inhibiting action.

At present, the only systematic method of fertility control available involves the administration of hormones or hormone-like substances to the female, generally to interfere with the normal menstrual or oestrous cycle. Considerable research has been undertaken to find an equivalent systematic method of fertility control in the male, so far without any real success. This research has generally been concerned with hormone-type action, although more recently attention has turned to the use of chemical substances having no hormonal affect, but instead possessing an entirely local action on the sperm.

One particular field of activity which is of considerable interest is intervention in the process of sperm maturation in the epididymis. This is an attractive approach to fertility regulation in the male since methods having this mechanism of action would not depress spermatogenesis or libido. Maturation of the sperm in the epididymis requires several days and the passage of the mature sperm through the epididymis lasts seven to twelve days, during which time the motility of the sperm is promoted. Thus, interference with this process can, in theory, produce immotile sperm which are hence non-fertile.

One substance which has previously been of considerable interest is racemic α-chlorohydrin. However this compound has recently been reported to have undesirable side effects and hence interest in racemic α-chlorohydrin has waned.

Our pending U.K. Patent Application No. 10694/77 describes and claims the use of certain 6-chloro-6-deoxysaccharides as antifertility agents believed to exert a depressant action on sperm motility.

We have now found that reduced analogues of 6-chloro-6-deoxy sugars possess activity of a similar nature.

According to the present invention, we provide a compound of the general formula:

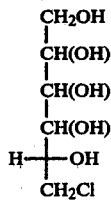
(I)

and physiologically acceptable esterified or other bio-labile forms thereof.

According to the present invention, we also provide a male fertility-inhibiting composition, in unit dosage form, containing as an active ingredient a compound of general formula (I) or a pharmacologically acceptable ester thereof in association with a pharmacologically acceptable carrier or excipient.

According to this invention, we also provide a method for preparing a compound of the general formula I comprising reacting a 6-chloro-6-deoxy-D-hexose of the general formula:

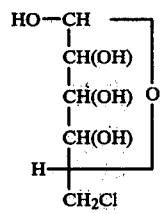
(II)

with a reducing agent capable of reducing an aldose to an alditol without dechlorination.

We also provide a male fertility-inhibiting composition containing a 6-chloro-6-deoxy-D-hexitol of the general formula:

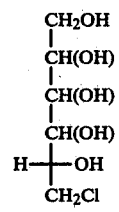
(I)

or a physiologically acceptable esterified or bio-labile form thereof together with a pharmaceutically acceptable carrier or excipient.

We also provide, as a further feature of this invention, a method of controlling the fertility of male animals, which term is taken to include fertility control in humans and also in the veterinary field, by administering thereto a compound of the formula (I) or a pharmacologically acceptable ester or bio-labile form thereof in an amount effective to control fertility.

The compound formula (I) is preferably a compound of the general formula:

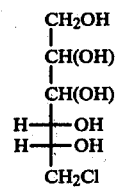
(Ia)

It will be understood that the Fischer projection formulae used herein represent compounds in the D-series.

According to convention, the bottom carbon atom carrying the chlorine atom constitutes the 6-position and the compound is in the D-series when the 5-hydroxy group is to the right. This corresponds to a 1-chloro substituted compound in the L-series. Thus, for example, 6-chloro-6-deoxy-D-glucitol is the same compound as 1-chloro-6-deoxy-L-gulitol:

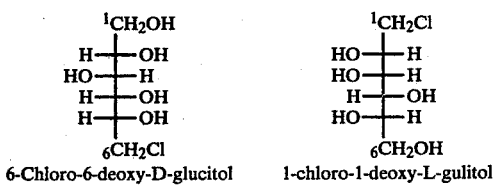

6-Chloro-6-deoxy-D-mannitol, on the other hand, is the same as 1-chloro-1-deoxy-D-mannitol:

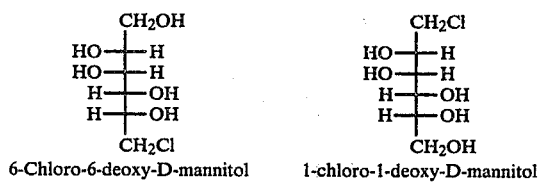

6-Chloro-6-deoxy-D-mannitol     1-chloro-1-deoxy-D-mannitol

It is conventional to use the lowest number for the substituted position, i.e. 1-chloro-1-deoxy-D-mannitol, rather than the 6-substituted-D-analogue. For consistency, however, compounds in this invention will be referred to throughout as 6-substituted D-series hexitols.

Compounds of particular interest are 6-chloro-6-deoxy-D-glucitol and 6-chloro-6-deoxy-D-mannitol. Also of interest is 6-chloro-6-deoxy-D-allitol, while 6-chloro-6-deoxy-D-galactitol is active, but less so.

The esterified derivatives thereof, according to the present invention, are preferably esters of aliphatic or aromatic carboxylic acids, e.g. acetates and benzoates. Per esters, in which all the hydroxyl groups are esterified (i.e. pentaesters), are particularly easily prepared, e.g. pentaacetates and pentabenzoates. Any ester, however, which can give the parent 6-chloro-6-deoxy-D-hexitol in vivo is suitable, as are other biolabile derivatives.

Compositions according to the present invention are preferably presented in a form for oral administration, such as tablets, coated tablets, capsules or soluble tablets. The presentation is conveniently adapted so that a dose of one or two units per day gives a sufficient level of protection. In general, each unit dosage may contain from 0.35 to 4.5 g, suitable for providing a daily dose of up to 60 mg/kg.

Other forms of administration envisaged may include slow-release or depot formulations, containing sufficient active ingredient per unit to suppress fertility for a sustained period.

The anti-fertility action of the compounds was demonstrated in a fertilisation test using rats according to the following method.

Groups of 6 or 8 male rats (CD strain, Charles River, Manston, Kent UK. 300–450 g body weight) were given 14 consecutive daily doses of 6-chloro-6-deoxyglucitol (60 or 90 or 120 or 240 μmol/kg/day) or 6-chloro-6-deoxy-mannitol (300 μmol/kg/day). Control groups were given water 1 ml/kg/day. The compounds were dissolved in water at concentrations such that the dose given was 1 ml/kg and they were administered by oral gavage.

Other male rats treated with 6-chloro-6-deoxy-glucitol pentaacetate (300 u mole/kg/day), which because it is not water soluble was administered by mixing it with powdered diet (Diet 86 Dixons, Ware, Hertfordshire, UK) which was then re-pelleted. These rats were supplied with the treated diet for at least 8 days. They were then transferred to cages where normal diet was supplied and they were paired with virgin females (CD strain Charles River, Manston, Kent. 180 g body weight) which were in the pro-oestrous stage of the oestrous cycle. Mating was confirmed by the presence of spermatozoa in vaginal smears. If mating did not occur after 2 days the male was returned to a cage supplied with treated diet for a further 2 days before a second attempt at mating. The mated females were treated as described below.

The male rats in the other groups were paired with virgin females (CD strain, 180 g body weight) for the second week of the dosing period. The females were killed 10 days after separation from the males and the embryos and resorbing embryos present in their uteri and the corpora lutea present in their ovaries were counted.

Some male rats which had been treated with 6-chloro-6-deoxyglucitol were killed on the day following their final dose and the ability of their spermatozoa to oxidise glucose was assessed as described by Ford and Waites, J. Reprod. Fert. 52, 153–157, (1978).

The results are summarised in the following Tables:

TABLE 1

The Antifertility Effect

| Compound | Dose (μmol/ kg/day) | No. of rats in group | No. pairings fertile | Implantations** | Corp. Lut/ female |
|---|---|---|---|---|---|
| Water (control) | 1 ml | 26* | 25 | 13.8 | 16.0 |
| 6-chloro-6-deoxy-glucitol | 60(= 12 mg) | 14* | 10 | 12.5 | 14.2 |
| | 90(= 18 mg) | 6 | 1 | 1 | 12.5 |
| | 120(= 24 mg) | 6 | 0 | 0 | 17.8 |
| | 240(= 48 mg) | 8 | 0 | 0 | 16.4 |
| 6-chloro-6-deoxy-glucitol pentaacetate | 300 (= 123 mg) | 6 | 0 | 0 | 16.7 |
| 6-chloro-6-deoxy-mannitol | 300 (= 60 mg) | 6 | 1 | 2 | 16.3 |

*Pooled data from more than on experiment
**Implantations and resorbing implantations/pregnant female.

TABLE 2

The Inhibition of glucose oxidation in spermatozoa from rats treated with 6-chloro-6-deoxyglucitol

| 6-chloro-6-deoxyglucitol μmol/kg/day | Glucose oxidation n mol [$U^{14}C$]-glucose converted to $^{14}CO_2/10^8$ spermatozoa/h |
|---|---|
| 0 | 8.8 ± 2.2 |
| 60 | 1.9 ± 0.5 |
| 90 | 0.5 ± 0.1 |
| 120 | 0.5 ± 0.1 |

Thus, 6-chloro-6-deoxy-D-glucitol showed complete anti-fertility activity at doses of 48, 24 and 18 mg/kg/day. The figure of 18 mg/kg/day compares favourably with the 24 mg/kg/day dose required for 6-chloroglucose. After 3 to 6 weeks without dosing, the fertility of the rats had returned.

6-Chloro-6-deoxy-D-glucitol possesses a low subacute toxicity and apparently does not inhibit glucose transport to the brain across the blood-brain barrier in rats. At doses of 240 mg/kg/day and 480 mg/kg/day for 28 days, mice showed toxic effects but recovered after the treatment was stopped.

As indicated above, the 6-chloro-6-deoxy D-hexitols of Formula I according to the present invention are novel compounds, as are their esterified derivatives, e.g. the acetates, especially the pentaacetates. They can be prepared by reduction of the corresponding 6-chloro-6-deoxy-D-aldose (Evans and Parrish, Methods in Carbohydrate Chemistry, 6, 193, 1972) by any convenient reducing system which will reduce an aldose to an alditol without dechlorinating it. A particularly preferred system is an alkali metal borohydride such as sodium borohydride in an inert polar solvent such as an alcohol or water. The reduced product is conveniently separated and purified in the form of its pentaacetate, prepared, for example, by treatment of the crude product with acetic anhydride either in pyridine or, preferably, in the presence of conc. sulphuric acid. The purified acetate may then be subjected to alcoholysis, for example by treatment with sodium methoxide in methanol, if the free hexitol is required.

The following Examples illustrate the invention.

EXAMPLE 1

6-Chloro-6-deoxy-D-glucitol

To a solution of 6-chloro-6-deoxy-D-glucose (20 g) in water (60 ml) at 5° C. was added dropwise, with stirring, a solution of sodium borohydride (4 g) in water (100 ml). The solution was kept at 5° C. for one hour, when t.l.c. showed the reduction to be complete. The solution was neutralized with acetic acid and evaporated to dryness (repeatedly with methanol). The residue was acetylated with acetic anhydride (100 ml) and conc. sulphuric acid (1 ml). 6-Chloro-6-deoxy-D-glucitol pentaacetate was obtained as a white crystalline solid (30 g) after recrystallisation from ethanol, m.p. 69° C.; $[\alpha]_D^{20}+19.5°$ (c=2.0; chloroform); T.l.c. $R_f$ 0.30 (pet. ether: EtOAc; 2:1) silica gel; Nmr spectrum (TMS as internal reference, in deuteriochloroform ($CDCl_3$)):

$\tau=4.50$ (multiplet; 2 protons; H-3,4), 4.78 (multiplet; 2 protons; H-2,5), 5.54 (quartet; 1 proton; H-1a), 5.88 (quartet; 1 proton; H-1b), 6.20 (quartet; 1 proton; H-6a), 6.38 (quartet; 1 proton; H-6b), 7.74 (singlet; 3 protons; one acetate group), 7.84 (singlet; 12 protons; four acetate groups).

The pentaacetate was suspended in methanol (100 ml) and sodium methoxide (1 M) was added to the cooled (5° C.) solution to pH 9. When reaction was complete, the product was isolated by neutralisation with Amberlyst 15 H+ resin (Trade Mark), filtration and evaporation to give 6-chloro-6-deoxy-D-glucitol as a colourless syrup (11 g, 55% overall) $[\alpha]_D^{20}=+6.0°$ (c=0.9; methanol) t.l.c. $R_f$ (silica gel)=0.30 (EtOAc: EtOH: $H_2O$; 45:5:1).

EXAMPLE 2

6-Chloro-6-deoxy-D-mannitol

6-Chloro-6-deoxy-D-mannose was reduced in the same manner as in Example 1 to give the 6-chloro-6-deoxy-D-mannitol. M.p. 115°-116° C.; $[\alpha]_D^{20}+3.5°$ (c=1.0, methanol); $R_f$ (t.l.c. silica gel; ethyl acetate:ethanol:water, 45:5:1) 0.24; NMR (in deuterated methanol ($CD_3OD$) relative to T.M.S.) $\tau=6.1$ (multiplet).

The pentaacetate gave the following NMR spectrum (in deuteriobenzene ($C_6D_6$) relative to T.M.S.):

$\tau=4.38$ (multiplet; 2 protons H-3,4), 4.72 (multiplet; 2 protons H-2,5), 5.70 (quartet; 1 proton H-1a), 5.92 (quartet; 1 proton H-1b), 6.40 (quartet; 1 proton H-6a), 6.65 (quartet; 1 proton H-6a), 8.14 (singlet; 6 protons 2 acetate groups), 8.16 (singlet; 3 protons 1 acetate group), 8.19 (singlet; 6 protons 2 acetate groups).

EXAMPLE 3

6-Chloro-6-deoxy-D-galactitol

Reduction of 6-chloro-6-deoxy-D-galactose by the method described in Example 1 gave 6-chloro-6-deoxy-D-galactitol, recrystallised from methanol. The product had m.p. 166°-167°; $[\alpha]_D^{20}+0.5°$ (c=1.0, water); $R_f$ (t.l.c. silica gel; n-butanol:ethanol:water, 5:3:2) 0.68. 6-Chloro-6-deoxy-D-galactitol pentaacetate, recrystallised from ethanol, had m.p. 125°-127°, $[\alpha]_D^{20}-12.0°$ (c 1.0, chloroform); $R_f$ (t.l.c. silica gel; petroleum ether-:ethyl acetate, 2:1) 0.50; NMR (deuteriochloroform, relative to T.M.S.)

$\tau$4.71 (multiplet; 4 protons, H-2,3,4,5), 5.73 (quartet; 1 proton, H-1a), 6.21 (quartet; 1 proton, H-1b), 6.56 (multiplet; 2 protons, H-6a,6b), 8.01 (singlet: 9 protons, 3 acetate groups), 8.04 (singlet; 3 protons, 1 acetate group), 8.11 (singlet; 3 protons, 1 acetate group).

EXAMPLE 4

6-Chloro-6-deoxy-D-allitol

(a) 6-Chloro-6-deoxy-D-allose

Partial acid hydrolysis of 1,2: 5,6-di-O-isopropylidene-α-D-allose (J. D. Stevens, in *Methods in Carbohydrate Chemistry*, 6, 123, 1972) (12 g) in 0.4% sulphuric acid (70 ml) and methanol (70 ml) overnight at room temperature gave, after neutralisation (Zerolit DM-F $H^+/CO_3{}^{2-}$) and evaporation, 1,2-O-isopropylidene-α-D-allose (8 g), recrystallised from methanol-ether, with m.p. 125°-128°. 1,2-O-Isopropylidene-α-D-allose (8 g) was selectively chlorinated (A. K. M. Anisuzzaman and R. L. Whistler, *Carbohydrate Research* 61, 511, 1978) using triphenylphosphine (18 g) and carbon tetrachloride (5 ml) in pyridine (100 ml) overnight at room temperature to give 6-chloro-6-deoxy-1,2-O-isopropylidene-α-D-allose (5.5 g) after column chromatography on silica gel (elution with ethyl acetate:petroleum ether, 9:1). The product was recrystallised from ether-petroleum ether and had m.p. 106°-108°; $[\alpha]_D^{20}+41.2°$ (c=2.0, chloroform); mass spectrum, m/$\epsilon$223 (M+ −15).

Acid hydrolysis (50 ml of 80% trifluoroacetic acid at room temperature for 15 min) of the 1,2-O-isopropylidene derivative (5 g) yielded 6-chloro-6-deoxy-D-allose (2.9 g) after recrystallisation from ethyl acetate. The product had m.p 135°-136°; $[\alpha]_D^{20}+10.7°$ (3 h; c=2.0, water); $R_f$ 0.71 (t.l.c. silica gel; n-butanol:ethanol:water, 5:3:2); analysis: found C 36.3, H 5.6, Cl 18.0; calculated C 36.3, H 5.6, Cl 17.9%.

(b) 6-Chloro-6-deoxy-D-allitol

6-Chloro-6-deoxy-D-allose was reduced by the method described in Example 1 to give 6-chloro-6-deoxy-D-allitol as a colourless syrup, $[\alpha]_D^{20}+5.3°$ (c=1.0, methanol); $R_f$ 0.72 (t.l.c. silica gel; n-butanol:ethanol:water, 5:3:2).

EXAMPLE 5

Tablets

6-Chloro-6-deoxy-D-glucitol is combined in a conventional manner with conventional tableting binders and lubricants and is pressed into tablets, each containing 2.0 g of the active ingredient.

EXAMPLE 6

Capsules

6-Chloro-6-deoxy-D-glucitol is combined with a conventional excipient or diluent and packed into gelatin capsules, each containing 2.0 g of the active ingredient.

We claim:

1. A male fertility-inhibiting composition containing an effective fertility-inhibiting amount of 6-chloro-6-deoxy-D-hexitol of the general formula:

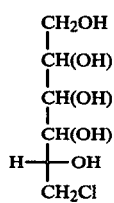

or a physiologically acceptable esterified form thereof together with a pmaceutically acceptable carrier or excipient.

2. A composition according to claim 1, in unit dosage form.

3. A composition according to claim 2, containing per unit 0.35 to 4.5 g of the said compound.

4. A composition according to claim 1, containing a compound of the general formula:

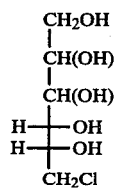

5. A composition according to claim 1, containing a compound selected from 6-chloro-6-deoxy-D-glucitol; 6-chloro-6-deoxy-D-mannitol; 6-chloro-6-deoxy-D-galactitol and 6-chloro-6-deoxy-D-allitol, and acetates and benzoates thereof.

6. A method of controlling fertility in male animals, comprising administering thereto a fertility-inhibiting effective amount of a compound of the general formula

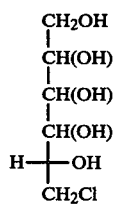

and physiologically acceptable esterified forms thereof.

* * * * *